(12) United States Patent
Risbridger et al.

(10) Patent No.: US 6,294,335 B1
(45) Date of Patent: Sep. 25, 2001

(54) METHOD OF DIAGNOSING ABNORMAL CELL GROWTH

(75) Inventors: Gail Petuna Risbridger, East Malvern; David Morritz De Kretser, Surrey Hills, both of (AU)

(73) Assignee: Monash University, Victoria (AU)

( * ) Notice: Subject to any disclaimer, the term of this patent is extended or adjusted under 35 U.S.C. 154(b) by 0 days.

(21) Appl. No.: 09/424,392

(22) PCT Filed: May 26, 1998

(86) PCT No.: PCT/AU98/00385

§ 371 Date: Jan. 24, 2000

§ 102(e) Date: Jan. 24, 2000

(87) PCT Pub. No.: WO98/54358

PCT Pub. Date: Dec. 3, 1998

(30) Foreign Application Priority Data

May 26, 1997 (AU) .................................................. PO7071

(51) Int. Cl.[7] ..................................................... C12Q 1/68
(52) U.S. Cl. .................... 435/6; 435/6; 435/69.1; 435/252.3; 435/254.11; 435/325; 435/320.1; 536/23.1; 536/23.5; 935/22
(58) Field of Search .......................... 435/6, 69.1, 252.3, 435/254.11, 325, 320.1; 536/23.1, 23.5; 935/22

(56) References Cited

PUBLICATIONS

Klein et al. Endocrinology. vol. 128, No. 2. pp 1048–1053.*
Madjic et al. Endocrinology. vol. 138 No. 5. pp. 2136–2147.*
Wang et al. "Activin Inhibits Basal and Androgen–Stimulated Proliferation and Induces Apoptosis in the Human Prostatic Cancer Cell Line, LNcAP" Endocrinology 137(12): 5476–5483 (1996).
Sakomoto et al. "Determination of Free Follistatin Levels in Sera of Normal Subjects and Patients with Various Diseases" European Journal of Endocrinology 135(3): 345–351 (1996).
Schaik et al. "Human testicular Germ Cell Tumours Express Inhibin Subunits, Activin Receptors and Follistatin mRNAs" British Journal of Cancer 76(9): 1191–1196 (1997).
Dalkin et al. "Activin Inhibition of Prostate Cancer Cell Growth: Selective Actions on Androgen–Responsive LNCaP Cells" Endocrinology 137(12): 5230–5235 (1996).
Penabad et al. "Decreased Follistation Gene Expression in Gonadotroph Adenomas" The Journal of Clinical Endocrinology and Metabolism 81(9): 3397–3408 (1996).

* cited by examiner

Primary Examiner—W. Gary Jones
Assistant Examiner—Janell E. Taylor
(74) Attorney, Agent, or Firm—Morrison & Foerster LLP (57) ABSTRACT

The present invention relates to a method of diagnosing a mammal having abnormal prostatic cell growth or a predisposition to developing abnormal prostatic cell growth, said method comprising screening for the modulation of the expression of follistatin protein or derivative, homolog, analog, mutant, variant or fragment thereof in said mammal. More particularly, the present invention contemplates a method of diagnosing prostate cancer or a predisposition to developing prostate cancer, said method comprising screening for the co-expression of different forms of follistatin protein.

11 Claims, 3 Drawing Sheets

METHOD OF DIAGNOSING ABNORMAL CELL GROWTH

The present invention relates generally to a method of diagnosing abnormal cell growth or a predisposition to abnormal cell growth. More particularly, the present invention contemplates a method of diagnosing abnormal prostatic cell growth or a predisposition to abnormal prostatic cell growth and even more particularly prostate cancer or a predisposition to developing prostate cancer.

The bibliographic details of the publications referred to by author in the specification are collected at the end of the description.

Throughout this specification, unless the context requires otherwise, the word "comprise", or variations such as "comprises" or "comprising", will be understood to imply the inclusion of a stated element or integer or group of elements or integers but not the exclusion of any other element or integer or groups of elements or integers.

Disorders of the prostate gland are of particular concern in ageing men. Figures suggest that approximately one in four males above the age of 55 will suffer from a prostate disease in some form. The incidence in Australia of prostatic cancer is high and similarly prevalent rates occur in most communities. This represents a significant cost to health care systems and decreases the quality of life of men suffering from this disorder.

Inhibins are glycoprotein hormones produced by the gonads which have a negative feedback action on the release of FSH from the pituitary gland. They consist of two disulphide linked subunits, $\alpha$ and either $\beta_A$ or $\beta_B$, which give rise to inhibin A or B respectively. Activins are formed by the dimerisation of two $\beta$ subunits. Three dimeric forms of activin have been published: activin A [$\beta_A$ $\beta_A$], activin B [$\beta_B$ $\beta_B$] and activin AB [$\beta_A$ $\beta_B$]. In contrast to inhibins, activins stimulate pituitary FSH (Ling et al., 1986).

Activins have been shown to have either proliferative or anti-proliferative actions in reproductive, neuroendocrine and erythroid tissues (Hedger et al.,1989, Mather et al., 1990, Nakao et al., 1991). The effects of activins on cultured cells include induction of cell cycle arrest (Kojima et al.,1993) and apoptosis (Nishihara et al., 1993). A further three activin $\beta$ subunits termed $\beta_C$–$\beta_E$ (Hotten et al., 1995, Oda et al., 1995, Fang et al., 1996) have been cloned, but the putative activin homo- and hetero-dimers from these subunits have yet to be isolated, purified, and their biological roles established.

Follistatins are structurally unrelated proteins (which also stimulate FSH secretion) (Robertson et al., 1987), but importantly follistatins bind activins and result in the neutralisation of activin bioactivity (Mather et al., 1993, Nishihara et al., 1993). Follistatins are glycosylated monomeric proteins that arise from two alternatively spliced mRNA (FS315 and FS288), resulting in three protein cores; nine molecular weight forms are postulated, based on alternative splicing, proteolytic cleavage, variable glycosylation, and six have been identified and characterised (Sugino et al., 1993).

It has been shown that inhibins, activins and follistatins are synthesised by the human prostate gland (Thomas et al., 1997a; 1997b).

Understanding the cellular localisation and expression of follistatin is required to determine the role of follistatin in prostate cancer. In work leading up to the present invention, the inventors discovered that whereas follistatin mRNA is detectable in both stromal and basal epithelial cells of the non-malignant prostate, in malignant prostate cells follistatin mRNA is expressed throughout the disordered epithelium. In contrast to follistatin mRNA expression, the follistatin proteins that are expressed are of different form in the stroma and basal epithelial prostate cells. Further, expression of said follistatin proteins is modulated in the transition from non-malignancy to malignancy resulting in the co-expression of at least 2 different forms of the follistatin proteins in the malignant cells and is therefore indicative that an individual has or will develop prostate cancer.

Accordingly, one aspect of the present invention relates to a method of diagnosing a mammal having abnormal prostatic cell growth or a predisposition to developing abnormal prostatic cell growth, said method comprising screening for the modulation of the expression of follistatin protein in said mammal.

The term "mammal" includes humans, primates, livestock animals (e.g. horses, cattle, sheep, pigs, donkeys), laboratory test animals (e.g. mice, rats, rabbits, guinea pigs), companion animals (e.g. dogs, cats) and captive wild animals (e.g. kangaroos, deer, foxes). Preferably, the mammal is a human or a laboratory test animal. Even more preferably, the mammal is a human.

The term "expression" refers to the synthesis of a peptide, polypeptide or protein utilising the mechanisms of transcription and translation of a nucleic acid molecule.

Reference hereinafter to "follistatin" should be read as including reference to all forms of follistatin and to all proteins belonging to the follistatin family of proteins and derivatives, homologs, analogs, mutants, variants and fragments thereof including, by way of example, the three protein cores and six molecular weight forms of follistatin which have been identified as arising from the alternatively spliced mRNAs FS315 and FS288 and including but not limited to fragments, derivatives, homologs, analogs, mutants and variants thereof. "Follistatin" should also be understood to include, for example, reference to any peptide, polypeptide or protein which exhibits homology to follistatin for example the proteins described by Patthy et al (1993) and Hohenester et al (1997) or any protein which comprises any one or more of the epitopes of follistatin. Preferably, said follistatin proteins are one or both of the forms of follistatin protein detected by, but not limited to, the OxB288 antibody (Madjic et al., 1997)and the AS#202 antibody (Klein et al., 1991).

More particularly, the present invention relates to a method of diagnosing a mammal having abnormal prostatic cell growth or a predisposition to developing abnormal prostatic cell growth, said method comprising screening for the modulation of the expression of one or both of the forms of follistatin protein detected by the OxB288 antibody and the AS#202 antibody.

The term "modulation" refers to changes in the expression of the follistatin proteins. This includes but is not limited to, up-regulation of the expression in a cell of one or more follistatin proteins which were not previously expressed by said cell, co-expression of two or more forms of follistatin proteins or up-regulation of the level of expression of one or more follistatin proteins in a cell. For example, in non-malignant prostatic basal cells which are located adjacent to high grade malignant prostatic cells, the form of follistatin protein detected by the OxB288 antibody is expressed while the form of follistatin detected by the AS#202 antibody is not. In said adjacent high grade malignant prostatic cells, both of the forms of follistatin proteins detected by the OxB288 antibody and the AS#202 antibody are expressed. Accordingly, a preferred method is to detect the co-expression of the forms of follistatin proteins detected by the OxB288 antibody and the AS#202 antibody. Changes in expression of follistatin proteins may be due, for example, to alternative splicing of follistatin mRNA.

According to this preferred embodiment, the present invention relates to a method of diagnosing a mammal having abnormal prostatic cell growth or a predisposition to developing abnormal prostatic cell growth, said method comprising screening for the co-expression of the forms of follistatin protein detected by the OxB288 antibody and the AS#202 antibody.

The phrase "abnormal cell growth" includes but is not limited to cell growth which, relative to normal cell growth, exhibits an increase or a decrease in the rate of cell division, an increase or a decrease in the number of cell divisions or an alteration in cellular differentiation. Altered cellular differentiation can be evidenced, for example, by altered cell surface protein expression. Preferably, said abnormal cell growth is increased cell divisions.

Accordingly, in a preferred embodiment the present invention relates to a method of diagnosing a mammal having increased prostatic cell divisions or a predisposition to developing increased prostatic cell divisions, said method comprising screening for the modulation of the expression of follistatin protein in said mammal.

Preferably, said modulation is co-expression of the forms of follistatin protein detected by the OxB288 antibody and the AS#202 antibody.

More preferably, said increased prostatic cell division is prostate cancer.

According to this most preferred embodiment, the present invention relates to a method of diagnosing a mammal having prostate cancer or a predisposition to prostate cancer, said method comprising screening for the co-expression of the forms of follistatin protein detected by the OxB288 antibody and the AS#202 antibody in said mammal.

Although not intending to limit the invention to any one theory or mode of action, the induction of malignant prostate tumour growth is predicated on the observation that co-expression of the forms of follistatin detected by the OxB288 antibody and the AS#202 antibody occurs in the malignant prostatic cells and not in the non-malignant prostatic epithelial cells. The form of follistatin detected by the AS#202 antibody is not expressed in non-malignant prostatic epithelial cells while the form of follistatin detected by the OxB288 antibody is expressed in non-malignant prostatic epithelial cells. Activin has antiproliferative actions however its activity can be neutralised by the formation of an inactive complex with follistatin. The co-localisation of activin and follistatin to malignant prostate cells implies that follistatin neutralises the bioactivity of the activin ligands in the cell. Since both activin and follistatin are produced in non-malignant prostate tissue, tumour cells from patients with high grade prostate cancer achieve resistance to the antiproliferative effects of activin through the production of different forms of follistatin proteins with different neutralising activities.

Accordingly, in a preferred embodiment the present invention relates to a method of diagnosing a mammal having prostate cancer or a predisposition to prostate cancer, said method comprising screening for the modulation of the expression of follistatin protein in prostate cells of said mammal.

Preferably, said modulation is co-expression of the forms of follistatin protein detected by the OxB288 antibody and the AS#202 antibody.

According to this most preferred embodiment the present invention relates to a method of diagnosing a mammal having prostate cancer or a predisposition to prostate cancer, said method comprising screening for the co-expression of the forms of follistatin protein detected by the OxB288 antibody and the AS#202 antibody in prostate cells of said mammal.

Screening of follistatin expression in a mammal can be achieved via one of several techniques including but in no way limited to:

(i) in situ hybridisation of prostate tissue with probes detecting follistatin mRNAs.

(ii) immunohistochemistry of prostate tissues utilising antibodies directed to follistatin proteins.

(iii) quantitative measurement of follistatin proteins in prostate tissue.

(iv) measurement of the follistatin proteins in bodily fluids (for example blood or urine) as an indicator, for example, of changes occuring in prostate tissue.

In one particularly preferred method, the target follistatin molecules in the biological sample are exposed to a specific antibody which may or may not be labelled with a reporter molecule. Depending on the amount of target and the strength of the reporter molecule signal, a bound target may be detectable by direct labelling with an antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention is further described by reference to the following non-limiting Figures and/or Examples.

In the Figures:

FIGS. 1A–F is a photographic representation of the localisation of $\beta_A$ subunit protein using the $\beta_A$ Groome antibody in non-malignant [FIG. 1A (×20 magnification) and FIG. 1B (×40)] and malignant [FIG. 1D (×20) and FIG. 1E (×40)] regions of prostate tissue. Arrows indicate positive immunoreactivity localised to the epithelial cell layer in the non-malignant regions [FIG. 1A and FIG. 1B]. No positive immunoreactivity as observed when the sections were treated with rabbit IgG [FIG. 1C (×20) and 1F (×20)].

FIGS. 1G–L is aphotographic representation of the localisation of $\beta_A$ subunit protein using the $\beta_A$ Salk antibody in the non-malignant regions [FIG. 1G (×20) and 1H (×40)]. Arrows indicate patches of immunoreactivity in the stroma [FIG. 1G] or epithelium [FIG. 1H]. Immunoreactivity for $\beta_A$ subunit protein in malignant tumour cells is shown in FIG. 1J (×20) and 1K (×40), control sections showed no positive immunoreactivity [FIG. 1I (×20) and 1L (×20)].

FIGS. 1M–P is a photographic representation of the expression of $\beta_A$ subunit mRRNA in non-malignant [FIG. 1M (×40)] and malignant [FIG. 1N (×40)] regions Arrows indicate mRNA expression in the epithelium and stroma [FIG. 1M]. Using a sense cRNA probe as a control, no mRNA was localised in either non-malignant [FIG. 1O (×20)] or malignant FIGS. 1P (×20)].

The Bar in FIG. 1A represents 100 $\mu$m in FIG. A, C, D, F, G, I, J, L, M, O, P. The Bar in FIG. 1B represents 50 $\mu$M in FIG. E, H, K, N.

FIGS. 2A–F is a photographic representation of the positive immunoreactivity using the Groome $\beta_B$ antibody in non-malignant [FIG. 2A (×20) and 2B (×40)] and malignant [FIG. 2D (×20) and 2E (×40)] regions of tissue. Arrows indicate positive immunoreactivity in basal cells in FIG. 2B. No immunoreactivity was observed in control sections [FIG. 2C (×20) and 2F (×20)].

FIGS. 2G–L is a photographic representation of the $\beta_B$ subunit protein using the Salk antibody, in non-malignant [FIG. 2G (×20) and 2H] and malignant regions [FIG. 2J (×20) and 2K (×40)]. Arrow indicates basal cell immunoreactivity [FIG. 2H]. No positive immunoreactivity was observed in control sections [FIG. 2I (×20 cells magnification) and 2L (×20)].

FIGS. 2M–P is a photographic representation of the localisation of $\beta_B$ mRNA in non-malignant regions [FIG. 1M (×40)] and malignant regions [FIG. 2N (×40)]. Arrow indicates mRNA expression in basal cells [FIG. 2M]. Using a sense cRNA probe as a control, no mRNA was localised [FIG. 20 (×20) and FIG. 2P (×20)]. Bar represents 100 $\mu$m in FIG. 2A, C, D, F, G, I, J, L, M, O, P. The Bar represents 50 $\mu$m in FIGS. 2B, E, H, K, N.

FIGS. 3A–F is a potographic representation of the follistatin immunoreactivity using AS#202 which was localised to non-malignant [FIG. 3A (×20) and 3B (×40)] and malignant [FIG. 3D (×20) and 3E (×40)] regions. Arrows indicate positive immunoreactivity in the stroma [FIG. 3A and 3B]. No positive immunoreactivity was observed in the controls [FIG. 3C (×20) and 3F (×20)].

FIGS. 3G–L is a photographic representation of FS288 immunoreactivity using OxB288. Immunoreactivity was observed in non-malignant regions [FIG. 3G (×20) and 3H (×40)] and malignant regions [FIG. 3J (×20) and 3K (×40)]. Arrows indicate positive immunoreactivity in the basal cells [FIG. 3G and 3H]. Positive immunoreactivity was not observed in the control sections [FIG. 3I (×20) and 3L (×20)].

FIG. 3M–P is a photographic representation of follistatin mRNA expression. Follistatin mRNA was expressed in the non-malignant [FIG. 3M (×40)] and malignant [FIG. 3N 40)] regions of tissue. Arrows indicate the basal and stromal cell expression in [FIG. 3M]. Using a sense cRNA probe, no mRNA was detected in non-malignant [FIG. 3O (×20)] or malignant [FIG. 3P (×20)] tissues. The Bar represents 100 $\mu$m in FIGS. 3A, C, D, F, G, I, J, L, M, O, P. The Bar represents 50 $\mu$m in FIGS. 3B, E, H, K, N.

EXAMPLE 1

Patient Samples

Needle biopsy specimens were obtained from a total of 25 patients undergoing TRUS-guided biopsy. Carcinoma of the prostate was confirmed by independent histologic examination (Melbourne Pathology, Collingwood Australia) and the patients selected were diagnosed with high grade prostate cancer with a Gleason score of between 7 and 10. The specimens were obtained in accordance with the requirements and approval of the Standing Committee for Human Ethics and Experimentation at Monash Medical Centre and Monash University. Three micron sections were cut from the specimens and used for immunohistochemistry and/or in situ hybridsation (shown in Table 1) as described below. The expression or localisation of inhibin $\beta$ subunits or follistatins was compared in non-malignant regions and malignant (Gleason grade 4 or 5) regions of the tissue sections.

EXAMPLE 2

Immunohistochemical Studies

Antibodies

Four monoclonal antibodies for the inhibin $\beta_A$ and $\beta_B$ subunit proteins were utilised for these studies. The $\beta_A$ and $\beta_B$ Salk polyclonal antibodies (Roberts et al., 1991) (a gift from Dr W Vale) were raised in rabbit against synthetic human $\beta_A$ and $\beta_B$ peptides, and affinity purified with the synthetic peptide to which they were raised, and have previously been utilised for immnunohistochemical localisation of activin subunits [Roberts et al 1991]. The $\beta_A$ and $\beta_B$ Groome monoclonal antibodies (Madjic et al., 1997) were raised against synthetic human $\beta_A$ or $\beta_B$ peptides, and have previously been used for the measurement of inhibin A and inhibin B.

Follistatin immumunoreactivity was determined using two antisera. Polyclonal AS#202 was raised in an intact adult male New Zealand rabbit to purified bovine 39kDa follistatin, and has been used for the specific measurement of follistatin in serum samples by radioimmunoassay [Klein et al., 1991]. On Western blot analysis, the cross-reaction of bovine follistatin with AS#202 was approximately 16 times greater than that with human recombinant FS288 per ng of protein [Prof de Krester, personal communication]. Preabsorption of AS#202 was achieved by incubating 1 µg of bovine follistatin with 25 µl 5 of 1:500 dilution of AS#202 overnight at 4° C. The mixture was centrifuged at 12,000 g, the supernatant collected and used accordingly.

The monoclonal OxB288 antibody was raised to human recombinant FS288.

Immunohistochemistry

Sections were dewaxed, rehydrated and placed in Target Retrieval Solution (Dako, Carpintaria, Calif.). Antigenic sites were exposed by microwaving the sections at 2.25 W/ml/min for 3 minutes followed by 0.3 W/ml/min for 3–5 minutes or 20 minutes at 2.25 W/ml/min (Akai MW-420 microwave, Akai Electric Co., Korea), the sections were then allowed to cool in the antigen retrieval solution for 20 minutes prior to washing in 0.01 M phosphate buffered saline (PBS, 10 mM phosphate buffer, 15 mM NaCl, pH 7.4). Endogenous peroxidase activity was removed with 3% $H_2O_2$ for 30 minutes. Sections were incubated with 0.2% Triton X-100 (Sigma Chemical Co., St Louis Mo.) for 10 minutes, prior to blocking in either 1% DIG blocking reagent (Boehringer Mannheim GmbH Biochemica, Germany) or CAS block (Zymed, San Francisco Calif.) +10% normal serum. The sections were incubated with the primary antibody overnight at 4° C. ($\beta_A$, $\beta_B$ and FS288) or at room temperature for 2 hours (AS#202), washed in PBS and incubated with either biotinylated anti-rabbit IgG (1:200, Salk antibodies and AS#202; Zymed San Francisco, Calif.) or biotinylated anti-mouse IgG (1:200, Groome antibodies; Vector Laboratories Burlingame, Calif.) at room temperature for 1 hour. The sections were washed in 0.01 M PBS and incubated for 1 hour with streptavidin (1:50; Vectastain Elite ABC Kit; Vector Laboratories, Burlingame, Calif.). Following further washes with 0.01 M PBS, peroxidase activity was detected using 3', 3' diaminobenzidine tetrahydrochlorate (DAB; Liquid DAB Substrate Kit, Zymed). The reaction was terminated in distilled water and the sections counterstained with Mayer's haematoxylin (Sigma Diagnostics, St Louis, Mo.) and Scott's Tap Water, dehydrated and permanently mounted with DPX (BDH, Poole, England).

EXAMPLE 3

In Situ Hybridisation Studies

Probe Synthesis

Digoxygenin (DIG) labelled riboprobes were prepared using the methods outlined in the Boehringer Mannheim riboprobe labelling kit. Sense and antisense cRNA probes were generated from rat inhibin $\beta_A$ and $\beta_B$ [Esch et al 1987] and rat follistatin [Michel et al 1990] partial clones (370 bp, 390 bp and 267 bp respectively). RNA polymerases and restriction enzymes were purchased from Promega, Wis. The amount of DIG-labelled cRNA was determined by comparison to a DIG-labelled RNA control (Boehringer Mannheim GmbH Biochemica, Germany) using dot-blot analysis.

Hybndisation

Sections were dewaxed using histolene (Fronine Pty Ltd., Riverview, Australia) and rehydrated through graded ethanols. Slides were treated with 0.2 M HCl, and then washed in DEPC-treated water (2×5 min). Sections were digested with proteinase K (Boehringer Mannheim GmbH Biochemica, Germany) for 30 minutes at 37° C. Following incubation in 0.2% glycine for 10 min at 4° C., sections were equilibrated in 0.1 M triethanolamine and acetylated in 0.25% acetic anhydride for 5 min. After rinising in DEPC-treated water, sections were prehybridised for a minimum of 30 min. Prehybridisation solution contains 3×SSC (1×SSC is 0.15M sodium chloride, 15 mM sodium citrate, pH7), 1×Denhart's solution, 50% deionised formamide, 66 mM phosphate buffer pH8, 1000 µg/ml herring sperm DNA and 200 µg/ml tRNA.

Sections were hybridised overnight at 42° C. in hybridisation buffer (prehybridisation solution plus 10% dextran sulfate) containing a predetermined concentration (200–1000 ng/ml) of riboprobe. Excess probe was removed by sequential 15 min washes in 2×SSC at room temperature, 1×SSC at 42° C., 2×SSC at 42° C. and finally either 0.1 or 0.5×SSC (depending on the probe employed) at 42° C.

Anti-Dig Detection

The tissues were briefly washed in buffer 1 (0.1M maleic acid 0.15 M sodium chloride, pH7.5) prior to anti-DIG antibody detection. Sections were blocked in 1% DIG blocking reagent (Boehringer Mannheim GmbH Biochemica, Germany) in buffer 1 for 30 minutes at room temperature. Anti-digoxygenin Fab fragments conjugated to alkaline phosphatase (Boehringer Mannheim GmbH Biochemica, Germany) were diluted to 1:1000 in 1% blocking reagent in buffer 1, and the sections were incubated for a minimum of 1 hour at room temperature. After rinising in buffer 1, alkaline phosphatase activity was detected using NBT/BCIP substrate (NBT/BCIP 1-step, Pierce, Il). The reaction was stopped by immersion in water, and the slides were mounted under glass coverslips using GVA histomount (Zymed, San Francisco, Calif.).

EXAMPLE 4

$\beta_A$ Expression and Localisation

Figure 1:
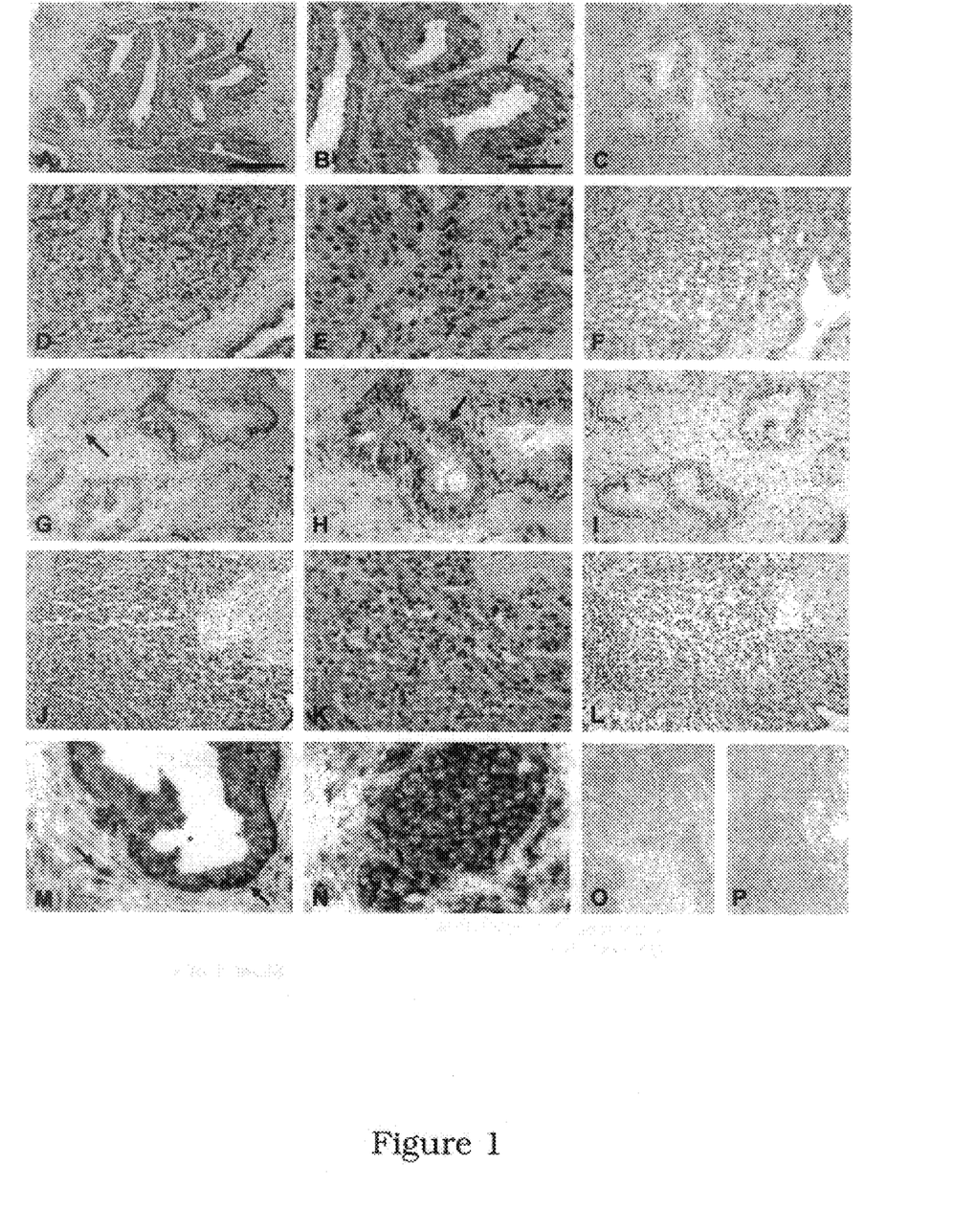
FIG. 1 is a photographic representation of the localisation and expression of $\beta_A$ subunit mRNA and protein in non-malignant and malignant regions of prostate tissues from men with high grade prostate cancer.

The pattern of immunostaining in the non-malignant and malignant regions of tumour tissue obtained from patients with advanced stage prostate cancer using two specific $\mu_A$ subunit antibodies is shown in FIG. 1. Using the $\beta_A$ Groome antibody, positive immunoreactivity was observed in the basal and secretory epithelial cells in the non-malignant regions of tissue (FIGS. 1A and B); intense immunoreactivity for $\beta_A$ subunit was also observed in tumour cells from adjacent regions of the tissue containing poorly differentiated tumour (FIGS. 1D and E). No immunostaining was observed in either the malignant or non-malignant regions of control sections (FIGS. 1C and F). Using the $\beta_A$ Salk antibody, a similar pattern of irmnunostaining was observed; the non-malignant epithelium showed positive immunoreactivity which was localised to the basal and secretory cells (FIGS. 1G and H, indicated by arrow) although the intensity of staining was highly variable. In addition, weaker stromal staining was observed in these non-malignant regions of the tissue sections as demonstrated by the arrows (FIGS. 1D and H). The malignant epithelial tumour cells showed consistent and positive staining of localisation for $\beta_A$ subunit protein (FIGS. 1J and K). No positive immunoreactivity was observed with rabbit IgG (FIGS. 1I and L).

In situ hybridisation confirmed that mRNA for $\beta_A$ subunit was present in the non-malignant regions of the sections from men with advanced stage prostate cancer which was predominantly localised to secretory and/or basal cells in the epithelium (FIG. 1M). Isolated groups of cells in the stroma also expressed $\beta_A$ mRNA (Arrows FIG. M). The expression of $\beta_A$ subunit mRNA was detected in the malignant cells of the adjacent regions of tumour tissue (FIG. 1N). Using the sense $\beta_A$ probe, no mRNA expression was detected (FIGS. 1O and P).

EXAMPLE 5

$\beta_B$ Subunit Expression and Localisation

Figure 2:
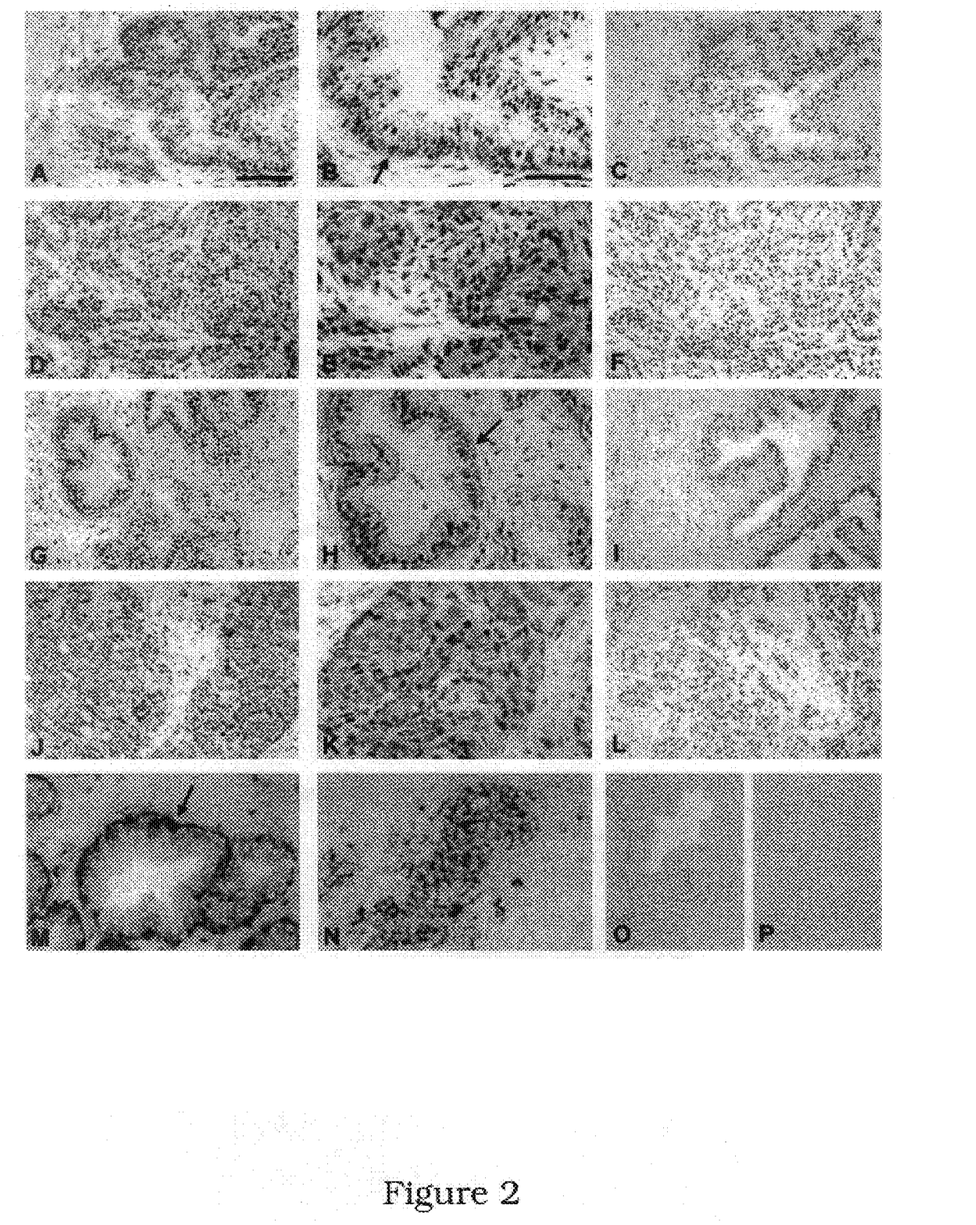
FIG. 2 is a photographic representation of the localisation and expression of $\beta_B$ subunit mRNA and protein in non-malignant and malignant regions of prostate tissues from men with high grade prostate cancer.

The pattern of expression and localisation for $\beta_B$ subunit is non-malignant and malignant regions of tissue obtained from patients with high grade prostate cancer is shown in FIG. 2. Using the $\beta_B$ Groome antibody, positive immunoreactivity was primarily localised to the epithelial compartment of non-malignant regions of tissue, with intense staining of $\beta_B$ subunit observed in the basal cells (FIGS. 2A and 2B). In adjacent malignant regions, immunoreactivity for $\beta_B$ subunit was localised to the tumour cells (FIGS. 2D and E), no positive immunostaining was observed in the controls sections (FIGS. 2C and F). Using the $\beta_B$ Salk antibody, imnunoreactivity was localised to the non-malignant epithelial tissue, and predominantly located in the basal, rather than the secretory epithelial cells (FIGS. 2G and H). Positive immunoreactivity for $\beta_B$ subunit was also present in the malignant tumour cells (FIGS. 2J and K). Positive immunoreactivity was not observed with rabbit IgG (FIGS. 2I and 2L).

mRNA for the $\beta_B$ subunit was expressed in the malignant and non-malignant epithelium; in the latter regions, the level of expression of $\beta_B$ subunit mRNA was greater in the basal cells when compared to the secretory epithelial cells and was consistent with the intense immunoreactivity in the basal cells using both of the $\beta_B$ antibodies (FIG. 2M). mRNA for $\beta_B$ subunit was also expressed in the tumour cells (FIG. 2N). No mRNA expression was detected using the $\beta_B$ sense probe in either malignant or non-malignant regions of the biopsy (FIGS. 2O and 2P).

EXAMPLE 6

The Localisation and Expression of Follistatin 202

Figure 3:
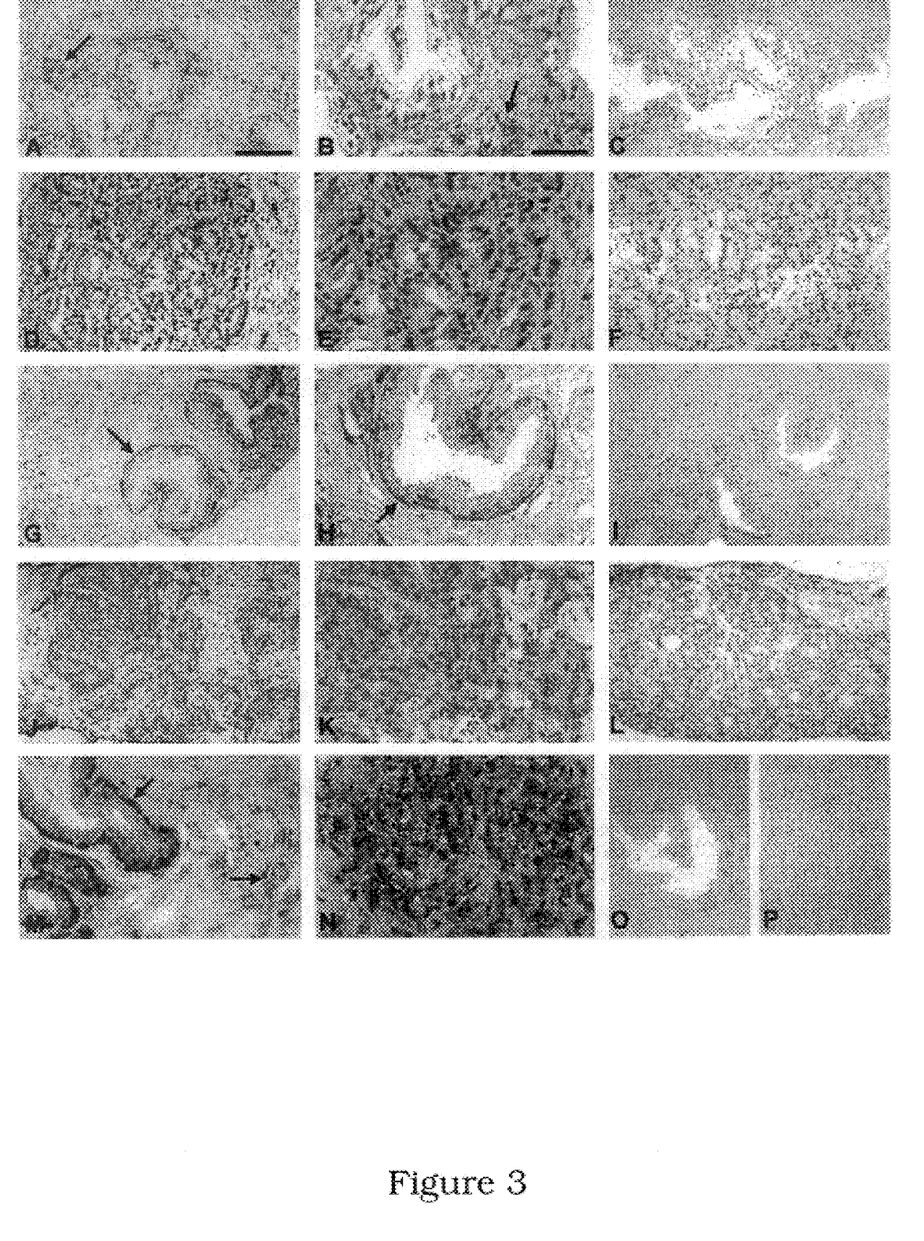
FIG. 3 is a photographic representation of the localisation and expression of follistatin submit mRNA and protein in non-malignant and malignant regions of prostate tissues from men with high grade prostate cancer.

Using the polyclonal antibody AS#202, follistatin immunoreactivity was localised to patchy regions of stromal tissue in the non-malignant regions of needle biopsies from men with advanced prostate cancer (FIGS. 3A and 3B). No immunoreactivity was observed in the epithelium, or in the control sections incubated with AS#202 preabsorbed with bovine follistatins (FIG. 3C). In contrast using the Groome FS 288 antibody, postive immunoreactivity was localised to the basal cells of the epithelium and was not recorded in surrounding stromal tissues (FIG. 3G and 3H). In the regions of poorly differentiated tumour, intense positive immunoreactivity was localised to the malignant epithelial cells (FIGS. D and E) using both FS antibodies (FIGS. 3D and 3E, FIGS. 3J and 3K). No positive localisation was observed with rabbit IgG (FIGS. 3F and 3L).

In the non-maglignant tissues, follistatin mRNA was expressed in patches of cells within the stromal tissue (FIGS. 3M and 3N), consistent with the immunoreactivity observed with AS#202 (FIGS. 3A and 3B). Follistatin mRNA was also expressed in the non-malignant epithelium, specifically in the basal cells (FIG. 3M); this site of expression of follistatin mRNA correlates with the detection of immunoreactivity for follistatin protein using Groome FS 288 Antibodies (FIGS. 3G and 3H). In the malignant tumour regions, follistatin mRNA was expressed in the tumour cells (FIG. 3N) which is consistent with the positive immunoreactivity that was recorded using both follistatin antibodies (FIGS. 3D, and 3E, FIGS. 3J and 3K). No mRNA expression was detected using the follistatin sense riboprobe (FIGS. 3O and 3P).

Those skilled in the art will appreciate that the invention described herein is susceptable to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

Analysis of patient samples from $\beta_A$, $\beta_B$, and follistatin proteins and mRNA by immunohistochemistry and in situ hybridization using specific antibodies and riboprobes

| Patient No. | Immunohistochemistry | | | | | | In Situ Hybridsation | | |
|---|---|---|---|---|---|---|---|---|---|
| | $\beta_A$ | $\beta_B$ | $\beta_A$ | $\beta_B$ | | | | | |
| # | Salk | Salk | Groome | Groome | AS#202 | FS288 | $\beta_A$ | $\beta_B$ | Follistatin |
| 1 | + | | + | | + | | | + | |
| 2 | | | | | + | | + | + | + |
| 3 | + | | + | + | + | | + | + | + |
| 4 | | | | | | | | + | + |
| 5 | | | | + | + | + | | + | + |
| 6 | + | + | + | + | + | | + | + | |
| 7 | | | | | | | | + | |
| 8 | | + | + | | + | | + | | + |
| 9 | + | + | + | + | + | | | | + |
| 10 | | + | + | + | + | + | + | | + |
| 11 | + | | | | + | | | | |
| 12 | + | | | | | | | | |
| 13 | | + | + | + | + | | + | | |
| 14 | | | | | + | | | | |
| 15 | | | | | + | | | | |
| 16 | | | | | + | | | | |
| 17 | | | | | + | | | | |
| 18 | | | | | + | | | | |
| 19 | | | | | | | | + | |
| 20 | | | | | | | | + | |
| 21 | | | | | | | | + | |

TABLE 1-continued

Analysis of patient samples from $\beta_A$, $\beta_B$, and follistatin proteins and mRNA by immunohistochemistry and in situ hybridization using specific antibodies and riboprobes

| Patient No. | Immunohistochemistry | | | | | | In Situ Hybridsation | | |
| --- | --- | --- | --- | --- | --- | --- | --- | --- | --- |
| | $\beta_A$ | $\beta_B$ | $\beta_A$ | $\beta_B$ | | | | | |
| # | Salk | Salk | Groome | Groome | AS#202 | FS288 | $\beta_A$ | $\beta_B$ | Follistatin |
| 22 | | | | | | + | | | |
| 23 | | | | + | + | + | | | |
| 24 | | | | | + | | | | |
| 25 | | | | | + | | | | |

+, Samples that were analysed for the expression and/or localisation of proteins.

BIBLIOGRAPHY

Fang, J., Yin, W., Smiley, E Wang S. Q., Bonadia, J., *Biochem. Biophys, Res. Comm.* 228:669–674, 1996.

Hedger, M. P., Drummond, A. E., Robertson, D. M., Risbridger, G. P., de Kretser, D. M., *Mol. Cell. Endocrinol.* 61:133–138, 1989.

Hohenester et. al., *EMBO J.* 16:3778–3786 (1997).

Hotten, G., Neidhardt., Schneider, C., Pohl, J., *Biochem. Biophys, Res. Comm.* 206:608–613, 1995.

Klein, R., Robertson, D. M., Shukovski, L., Findlay, J. K., de Kretser, D. M., *Endocrinol.* 128:1048–1056, 1991.

Kojima, I., Mogami, H., Shibata, H., *J. Endocrinol.* 137:99–105, 1991.

Ling, N., Ying, S-Y., Ueno, N., Simasaki, S., Esch, F., Hotta, M., Guillemin, R., *Nature.* 321:779–782, 1986.

Madjic, G., McNeilly, A. S., Sharpe, R. M., Evans, L. W., Groome, N. P., *Endocrinol.* 138:2136–2147, 1997.

Mather, J. P., Attie, K. M., Woodruff, T., Rice, G. C., Phillips, D. M., *Edocrinol.* 127:3206–3214, 1990.

Mather, J. P., Roberts, P. E., Krummen, L. A., *Endocrinol.* 132:2732–2734, 1993.

Nakao, K., Kosaka, M., Saito, S., *Exp Hematol.* 19:1090–1095, 1991.

Nishihara, T., Okahashi, N., Ueda, N., *Biochem. Biophys, Res. Comm.* 197:985–991, 1993.

Oda, S., Nishimatsu, S-I., Murakami, K., Ueno, N., *Biochem. Biophys, Res. Comm.* 210:581–588, 1995.

Patthy et al., *Trends in Neuroscience.* 16:76–81 (1993)

Roberts, V., Meunier, H., Sawchenko, P. E., Vale, W., *Endocrinol.* 1252350–2359.

Robertson, D. M., Klein, R., de Vos, F. L., et al., *Biochem. Biophys, Res. Comm.* 149:744–749, 1987.

Sugino, K., Kurosawa, N., Nakamura, T., et al., *J. Biol. Chem.* 268:15579–15587, 1993.

Thomas, T. Z., Wang, H., Chapman, S., et al., *Prostate.* 34:3443 (1997a).

Thomas, T. Z., Wang, H., Niclasen, P., O'Bryan, M. K., Evans, L. W., Groome, N. P., Pederson, J., and Risbridger, G. P., *J. Clin. Endocrin.* 82:3851–3857 (1997b).

What is claimed is:

1. A method of diagnosing a mammal having abnormal prostatic cell growth or a predisposition to developing abnormal prostatic cell growth, said method comprising screening for the modulation of the expression of follistatin protein or functional derivative, homolog, analog, mutant, variant or fragment thereof in said mammal.

2. A method of diagnosing a mammal having increased prostatic cell divisions or a predisposition to developing increased prostatic cell divisions, said method comprising screening for the modulation of the expression of follistatin protein or functional derivative, homolog, analog, mutant, variant or fragment thereof in said mammal.

3. A method of diagnosing a mammal having prostate cancer or a predisposition to prostate cancer, said method comprising screening for the modulation of the expression of follistatin protein or functional derivative, homolog, analog, mutant, variant or fragment thereof in the prostate of said mammal.

4. The method according to any of claims 1 or 2 or 3 wherein said screening comprises the in situ hybridisation of prostate tissue with oligonucleotide probes detecting follistatin mRNA.

5. The method according to any of claims 1 or 2 or 3 wherein said screening comprises the immunohistochemical analysis of prostate tissue utilising antibodies directed to follistatin protein.

6. The method according to any of claims 1 or 2 or 3 wherein said screening comprises the detection of follistatin protein in bodily fluid.

7. The method according to claim 6 wherein said bodily fluid is blood.

8. The method according to any one of claims 1, 2 or 3, which comprises screening for the modulation of the expression of one of the forms of follistatin protein detected by the OxB288 antibody or the AS#202 antibody.

9. The method according to any one of claims 1, 2 or 3, which comprises screening for the modulation of the expression of both of the forms of follistatin protein detected by the OxB288 antibody and the AS#202 antibody.

10. The method according to any one of claims 1, 2 or 3, which comprises screening for the modulation of the co-expression of the forms of follistatin protein detected by the OxB288 antibody and the AS#202 antibody.

11. The method according to any one of claims 1, 2 or 3, wherein the mammal is a human.

* * * * *

UNITED STATES PATENT AND TRADEMARK OFFICE
CERTIFICATE OF CORRECTION

PATENT NO. : 6,294,335 B1
DATED : September 25, 2001
INVENTOR(S) : Gail Petuna Risbridger et al.

It is certified that error appears in the above-identified patent and that said Letters Patent is hereby corrected as shown below:

Title page,
Item [73], Assignee, change "Monash University, Victoria (AU)" to -- Montech Pty Ltd., Victoria (AU) and Prostate Pty Ltd., Victoria (AU). --

Signed and Sealed this

Twenty-third Day of April, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.     : 6,294,335 B1
DATED          : September 25, 2001
INVENTOR(S)    : Gail Petuna Risbridger et al.

It is certified that error appears in the above-identified patent and that said Letters Patent is hereby corrected as shown below:

<u>Title page,</u>
Item [73], Assignee, change "Monash University, Victoria (AU)" to -- Prostate Diagnostics Pty Ltd., Victoria (AU). --

Signed and Sealed this

Twenty-ninth Day of July, 2003

*Director of the United States Patent and Trademark Office*